United States Patent
Papini et al.

(10) Patent No.: US 10,605,776 B2
(45) Date of Patent: Mar. 31, 2020

(54) POWER SYSTEMS AND METHODS FOR A PIPELINE INSPECTION APPARATUS

(71) Applicant: General Electric Company, Schenectady, NY (US)

(72) Inventors: Francesco Papini, Garching b. Munchen (DE); Alexander Felix Fiseni, Garching b. Munchen (DE); Christoph Boeld, Garching b. Munchen (DE)

(73) Assignee: General Electric Company, Schenectady, NY (US)

( * ) Notice: Subject to any disclaimer, the term of this patent is extended or adjusted under 35 U.S.C. 154(b) by 335 days.

(21) Appl. No.: 15/180,956

(22) Filed: Jun. 13, 2016

(65) Prior Publication Data
US 2017/0356880 A1    Dec. 14, 2017

(51) Int. Cl.
| | |
|---|---|
| G01N 27/82 | (2006.01) |
| H02K 17/42 | (2006.01) |
| F17D 5/06 | (2006.01) |
| F17D 5/00 | (2006.01) |

(52) U.S. Cl.
CPC .............. *G01N 27/82* (2013.01); *F17D 5/00* (2013.01); *F17D 5/06* (2013.01); *H02K 17/42* (2013.01)

(58) Field of Classification Search
CPC .. G01N 27/82; F17D 5/00; F17D 5/06; H02K 17/42
See application file for complete search history.

(56) References Cited

U.S. PATENT DOCUMENTS

| | | | |
|---|---|---|---|
| 5,347,186 A | 9/1994 | Konotchick | |
| 5,818,132 A | 10/1998 | Konotchick et al. | |
| 7,210,364 B2 | 5/2007 | Ghorbel et al. | |
| 7,309,934 B2 | 12/2007 | Tu et al. | |
| 8,358,134 B1 | 1/2013 | Hoyt | |
| 9,030,195 B2 | 5/2015 | Gies | |
| 2003/0164698 A1* | 9/2003 | Paulson | G01N 27/82 324/220 |
| 2010/0253093 A1 | 10/2010 | MacDonald et al. | |

(Continued)

OTHER PUBLICATIONS

Jung, S.Y., et al., "Performance Evaluation of Permanent Magnet Linear Generator for Charging the Battery of Mobile Apparatus," IEEE International Electric Machines and Drives Conference, pp. 516-521 (2001).

(Continued)

*Primary Examiner* — Jermele M Hollington
*Assistant Examiner* — Feba Pothen
(74) *Attorney, Agent, or Firm* — Mintz Levin Cohn Ferris Glovsky and Popeo, P.C.

(57) ABSTRACT

Systems and methods are provided for powering a pipeline inspection system. The system includes an induction generator extending along a radially curved plane. The induction generator having an outer surface and an opposing inner surface. The outer surface is positioned proximate to an inner surface area of a pipeline. The system also includes a controller circuit configured to generate a plurality of periodic waveform signals. The plurality of periodic waveform signals are received by the induction generator. The induction generator is configured to generate active power that charges an electric power source based on the plurality of periodic waveform signals and the inner surface area.

12 Claims, 5 Drawing Sheets

(56) References Cited

U.S. PATENT DOCUMENTS

| | | |
|---|---|---|
| 2012/0038354 A1 | 2/2012 | Gies |
| 2012/0104877 A1 | 5/2012 | Isaacs |
| 2013/0025370 A1 | 1/2013 | Herron et al. |
| 2013/0062881 A1 | 3/2013 | Mellah |
| 2014/0266009 A1 | 9/2014 | Comello et al. |
| 2014/0312890 A1* | 10/2014 | Di Lullo ............... G01N 27/82 324/240 |
| 2016/0126805 A1 | 5/2016 | Fiseni et al. |

OTHER PUBLICATIONS

International Search Report and Written Opinion issued in connection with corresponding PCT Application No. PCT/US2017/37313 dated Oct. 4, 2017.

Bouallaga et al.; A system for charging of dual voltage level batteries in automotive applications; 2007 IEEE International Electric Machines & Drives Conference; May 3-5, 2007;vol. 1 pp. 107-111.

* cited by examiner

POWER SYSTEMS AND METHODS FOR A PIPELINE INSPECTION APPARATUS

FIELD

Embodiments of the present disclosure relate to a pipeline inspection system, and more particularly to systems and methods that power the pipeline inspection system.

BACKGROUND

Pipelines carry a pressurized fluid, such as hydrocarbon gases and oils, slurries, water, and/or the like for many times hundreds of kilometers between pumping stations. The pipeline may be exposed to extreme weather that includes a corrosive atmosphere, exposed to alkaline or acidic content in the soil, manufacturing defects, and/or the like. Additionally, the contents carried within the pipeline may not be benign, but may be corrosive and/or abrasive.

It is known in the art to monitor the conditions of the pipelines by passing a pipeline inspection system (PIS) commonly known as a "pig" within the pipeline. The PIS includes sensors and recording devices that monitor the pipelines for any defects. The components of the PIS are supplied power by one or more electric power sources, such as batteries. Alternatively, a separate pig housing only batteries may be electrically coupled to the PIS to provide power to the PIS within the pipeline.

Conventionally, when inspecting the interior of the pipeline, the flow of the medium being transported is used to drive forward the PIS within the pipeline. Due to the length of the pipeline (in many cases hundreds of kilometers), the electric power sources must provide a charge to the PIS during the entire length of the pipeline. Thus, large portions of the PIS are dedicated to housing the batteries, which can increase the size and/or diameter of the PIS limiting which pipelines the PIS may traverse through. Additionally, the amount of charge of the battery limits the range of pipelines that can use the PIS.

BRIEF DESCRIPTION

In an embodiment a system (e.g., a pipeline inspection system) is provided. The system includes an induction generator extending along a radially curved plane. The induction generator having an outer surface and an opposing inner surface. The outer surface is positioned proximate to an inner surface area of a pipeline. The system also includes a controller circuit configured to generate a plurality of periodic waveform signals. The plurality of periodic waveform signals are received by the induction generator. The induction generator is configured to generate active power that charges an electric power source based on the plurality of periodic waveform signals and the inner surface area.

In an embodiment a method (e.g., for powering a pipeline inspection system) is provided. The method includes determining a forward velocity of a pipeline inspection system (PIS) traversing within a pipeline, calculating at least one of a frequency, voltage, or current of a plurality of periodic waveform signals based on the forward velocity, and generating the plurality of periodic waveform signals. The plurality of periodic waveform signals are received by an induction generator. The induction generator extending along a radially curved plane. The induction generator having an outer surface and an opposing inner surface. The outer surface is positioned proximate to an inner surface area of the pipeline. The method further includes receiving an active power from the induction generator. The active power is based on the plurality of periodic waveform signals and the inner surface area. The method also includes utilizing at least a portion of the active power to charge an electric power source of the PIS.

In an embodiment a system (e.g., a pipeline inspection system) is provided. The system includes a support structure, and a plurality of vessels mechanically attached to the support structure. At least one of the vessels having a sensor unit configured to measure a forward velocity of a pipeline inspection system (PIS). The system includes a power system mechanically attached to the support structure. The power system having an induction generator extending along a radially curved plane. The induction generator having an outer surface and an opposing inner surface. The outer surface is positioned proximate to an inner surface area of a pipeline. The power system further includes a controller circuit configured to generate a plurality of periodic waveform signals. The plurality of periodic waveform signals are received by the induction generator. The induction generator is configured to generate active power that charges an electric power source based on the plurality of periodic waveform signals and the inner surface area.

DETAILED DESCRIPTION

Figure 1:
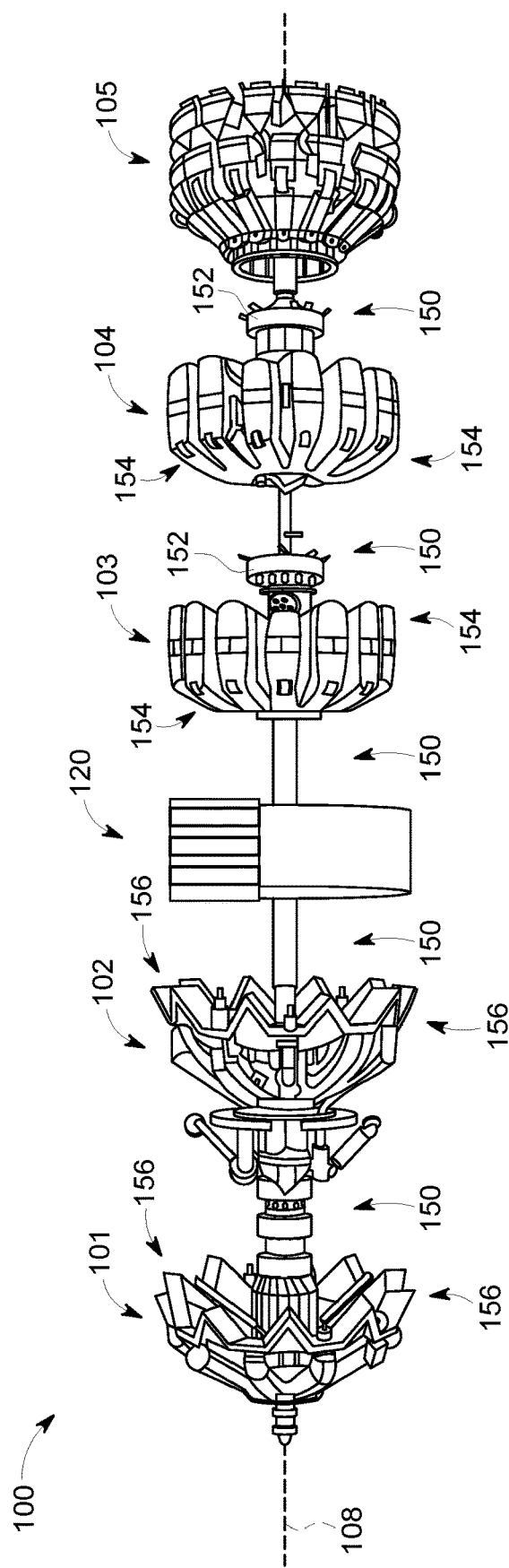
FIG. 1 illustrates a pipeline inspection system, in accordance with an embodiment.

Various embodiments will be better understood when read in conjunction with the appended drawings. To the extent that the figures illustrate diagrams of the functional blocks of various embodiments, the functional blocks are not necessarily indicative of the division between hardware (including circuitry). Thus, for example, one or more of the functional blocks (e.g., processors, controllers or memories) may be implemented in a single piece of hardware (e.g., a general purpose signal processor or random access memory, hard disk, or the like) or multiple pieces of hardware. Similarly, any programs may be stand-alone programs, may be incorporated as subroutines in an operating system, may be functions in an installed software package, and the like. It should be understood that the various embodiments are not limited to the arrangements and instrumentality shown in the drawings. The sizes of the components shown in the drawings may not be to scale and/or may have different aspect ratios.

As used herein, the terms "system," "circuit," "unit," or "device" may include a hardware and/or software system that operates to perform one or more functions. For example, a device, unit, circuit, or system may include one or more computer processors, microprocessors, field programmable gate arrays, integrated circuits, controllers, or other logic-based devices that perform operations based on instructions stored on a tangible and non-transitory computer readable storage medium, such as a computer memory. Alternatively, a device, unit, circuit, or system may include a hard-wired device that performs operations based on hard-wired logic of the device. The device, circuits, or units shown in the attached figures may represent the hardware that operates based on software or hardwired instructions, the software that directs hardware to perform the operations, or a combination thereof. The hardware may include electronic circuits that include and/or are connected to one or more logic-based devices, such as microprocessors, processors, controllers, or the like. These devices may be off-the-shelf devices that are appropriately programmed or instructed to perform operations described herein from the instructions described above. Additionally or alternatively, one or more of these devices may be hard-wired with logic circuits to perform these operations.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

One or more embodiments of the inventive subject matter described herein provides power systems and methods for a pipeline inspection system (PIS). The systems and methods extract kinetic energy from the moving PIS to recharge the electric power source (e.g., one or more batteries) of the PIS. For example, the PIS traverses within a pipeline at a forward velocity. The PIS is propelled by the pressurized fluid (e.g., hydrocarbon gases and oils, slurries, water, and/or the like) within the pipeline. A structure of the pipeline can be comprised of an electrically conductive material such as aluminum, steel, copper, and/or the like. The power system of the PIS may include an induction generator, such as a linear induction generator, positioned proximate to the pipeline. The power system is configured to power the induction generator, which creates a magnetic field. The magnetic field generates eddy currents in the pipeline, which generates a force opposed to the forward velocity of the PIS. The forward velocity of the PIS generates active power within the induction generator, which is delivered to the electric power source. For example, the active power is utilized by the power system to charger the batteries of the PIS.

A technical effect of at least one embodiment herein includes reducing an amount of batteries for the PIS. A technical effect of at least one embodiment herein includes augmenting and/or extending the operational time of the PIS within the pipeline.

FIG. 1 illustrates a pipeline inspection system (PIS) 100, in accordance with an embodiment. The PIS 100 is shown having a generally cylindrical structure. For example, the PIS 100 has a length extending along an axis 108 that is greater than a diameter of the PIS 100. The PIS 100 includes a plurality of vessels 101-105 and a power system 120. At least a portion of the vessels 101-105 may be configured to acquire information of a pipeline. For example, the vessels 103 and 104 may include a plurality of sensor units 154 movably mounted to the surface area of the vessels 103, 105. The sensors units 154 may be ultrasonic sensors, temperature sensors, flow sensors, pressure sensors, and/or the like configured to measure one or more characteristics of the pipeline and/or the fluid traversing within the pipeline. Additionally or alternatively, the sensor units 154 may be speed sensors, positional sensors (e.g., GPS), and/or the like configured to measure a one or more characteristics (e.g., a forward velocity) of the PIS 100.

Additionally or alternatively, a portion of the vessels 101-105 may be configured to guide the PIS 100 within the pipeline. For example, the vessels 101 and 102 may include a plurality of guiding flaps 156 (e.g., skirts, wipers, cups, and/or the like) which may be made of a material such as polyurethane. As the PIS 100 traverses within the pipeline the guiding flaps 156 deflect rearwardly, the outer peripheral edge of the guiding flaps 156 to be elastically biased to ride against the inside of the pipeline wall. For example, the guiding flaps 156 may be configured to maintain a distance and/or gap between the PIS 100 and the wall of the pipeline as the PIS 100 traverses within the pipeline. The guiding flaps 156 may be semi flexible plastic discs that are designed to seal against the pipeline wall, which allow the pressure of the fluid within the pipeline to drive and/or propel the PIS 100 through the pipeline.

The plurality of vessels 101-105 and the power system 120 are mechanically attached and/or fastened to a support structure 150 to form the PIS 100. For example, the support structure may extend through each of the vessels 101-105 and the power system 120 along a length of the PIS 100. The support structure 150 may include one or more pivot points 152. The pivot points 152 may be configured to allow portions of the support structure 150 to be radially displaced with respect to the axis 108. For example, as the PIS 100 traverses within a curve of the pipeline, the pivot points 152 allow the PIS 100 to conform to the pipeline. The support structure 150 may house one or more electrical conductors, such as wires or cables, to electrically couple one or more vessels 101-105 to the power system 120. For example, the power system 120 may deliver power (e.g., current, voltage) to one or more of the vessels 101-105 via the electrical conductors of the support structure 150. In another example, the power system 120 may receive one or more sensor measurements from the vessels 101-105 via the electrical conductors of the support structure 150. Optionally, the power system 120 may be configured to record the sensor measurements acquired by the PIS 100 in memory (e.g., the memory 206).

Figure 2:
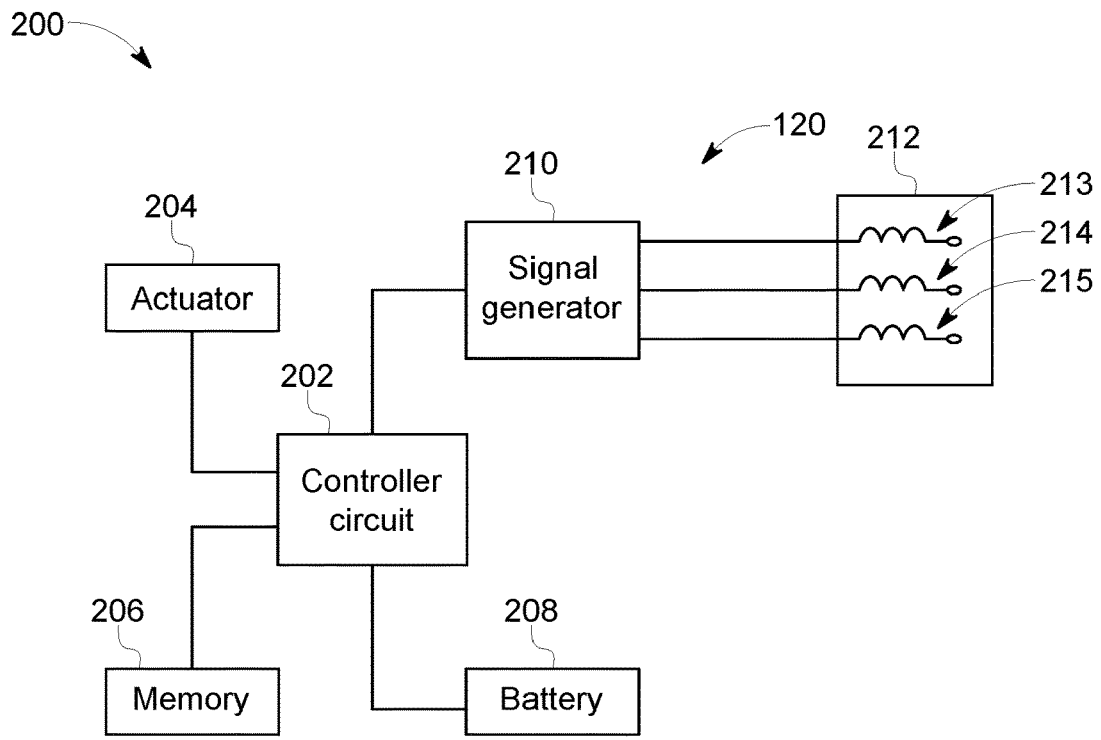
FIG. 2 illustrates a schematic block diagram of a power system of the pipeline inspection system shown in FIG. 1, in accordance with an embodiment.

FIG. 2 illustrates a schematic block diagram 200 of the power system 120 of the PIS 100, in accordance with an embodiment. The power system 120 may include a controller circuit 202 configured to control the operation of the power system 120. The controller circuit 202 may include and/or represent one or more hardware circuits or circuitry that include, are connected with, or that both include and are connected with one or more processors, controllers, or other hardware logic-based devices. Additionally or alternatively, the controller circuit 202 may execute instructions stored on a tangible and non-transitory computer readable medium (e.g., memory 206) to perform one or more operations as described herein.

The power system 120 includes an electric power source, such as one or more batteries 208. The batteries 208 may be a lithium ion battery, lead-acid battery, nickel cadmium battery, and/or the like. The batteries 208 may be electrically coupled to windings 213-215 (e.g., coils) of an induction generator 212, which allow active power generated by the induction generator 212 to be received by the batteries 208. For example, the active power received by the batteries 208 is utilized to charge the batteries 208.

Optionally, the active power is converted based on a predetermined electrical specification (e.g., a charging current, a charging voltage) that define electrical characteristics to charge the batteries 208. The predetermined electrical specification may be stored in the memory 206. For example, the predetermined electrical specifications may define a set of voltage and/or current parameters for charging the batteries 208. The conversion of the active power to the predetermined electrical specifications may be based on electrical charging circuitry (not shown) interposed between the batteries 208 and the induction generator 212. For example electrical charging circuitry may include a capacitor bank, an inverter, a rectifier, one or more capacitors, a buck converter, and/or the like.

The controller circuit 202 may be electrically coupled to a signal generator 210. The signal generator 210 may be configured to generate a plurality of periodic waveforms that are received by the inductor generator 212. The plurality of periodic waveforms may be a digital signal (e.g., square wave) and/or analog signal (e.g., sine wave). The electrical characteristics (e.g., frequency, amplitude) of the periodic waveforms may be defined by the controller circuit 202. It may be noted in other embodiments, the signal generator 210 may be integrated with and/or apart of the controller circuit 202. For example, the operations of the signal generator 210 are performed by the controller circuit 202.

Each periodic waveform is delivered to a corresponding winding 213-215 of the induction generator 212, and have a different phase with respect to each other such that each of the periodic waveforms are offset with respect to each other (e.g., three phase system). For example, the periodic waveform delivered to the winding 214 is offset relative to the periodic waveform delivered to the winding 213 by one third of the period of the periodic waveforms. In another example, the periodic waveform delivered to the winding 215 is offset relative to the periodic waveform delivered to the winding 214 by one third of the period of the periodic waveforms and the periodic waveform delivered to the winding 213 by two thirds of the period of the periodic waveforms.

Figure 3:
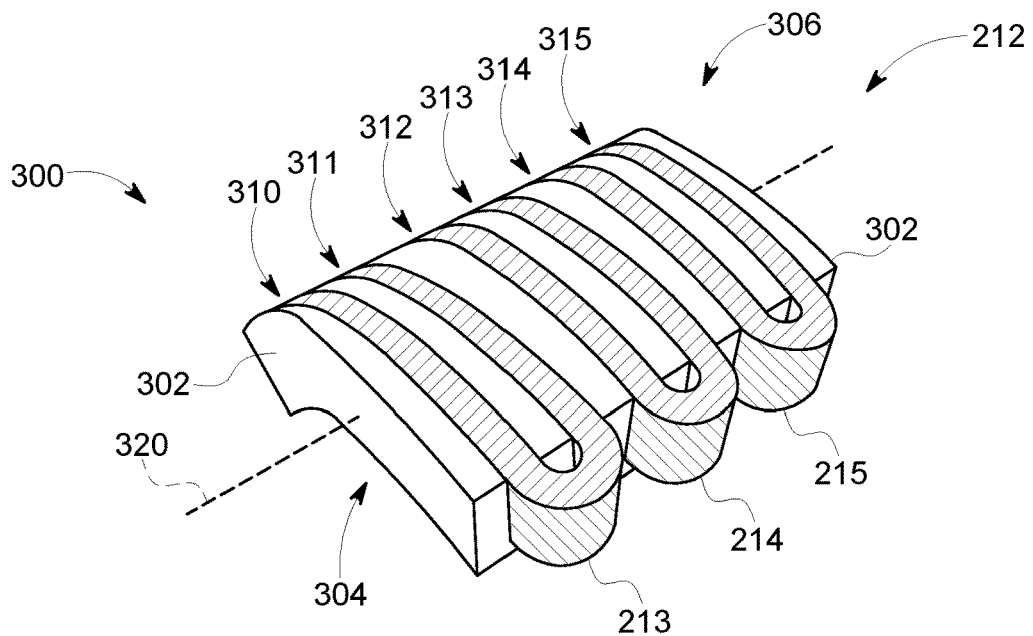
FIG. 3 illustrates a peripheral view of an induction generator of the power system shown in FIG. 2, in accordance with an embodiment.

In connection with FIG. 3, the periodic waveforms delivered to the windings 213-215 may be configured to generate a force opposed to a forward motion and/or velocity of the PIS 100. For example, the waveforms may be utilized by the controller circuit 202 to generate a magnetic field emitted by the induction generator 212, which passes a magnetic flux to the pipeline creating the opposing force of the PIS 100.

FIG. 3 illustrates a peripheral view 300 of the induction generator 212 of the power system 120, in accordance with an embodiment. The induction generator 212 includes a magnetic core 302, such as electrical steel, and/or the like. The magnetic core 302 having a length extending along an axis 320 and a width aligned along a radially curved plane (e.g., radially curved plane 412 of FIG. 4). The magnetic core 302 includes a series of grooves 310-315 along an outer surface 306 of the induction generator 212. The grooves 310-315 may be configured to fasten and/or allow the windings 213-215 to be positioned at least partially within the magnetic core 302. Additionally, the grooves 310-315 may define a pole pitch of the induction generator 212 corresponding to the distance between two adjacent poles of the induction generator 212. In connection with FIG. 4, the magnetic core 302 may be configured to extend along the radially curved plane 412 that conforms to an inner surface area 410 of the pipeline 402.

Figure 4:
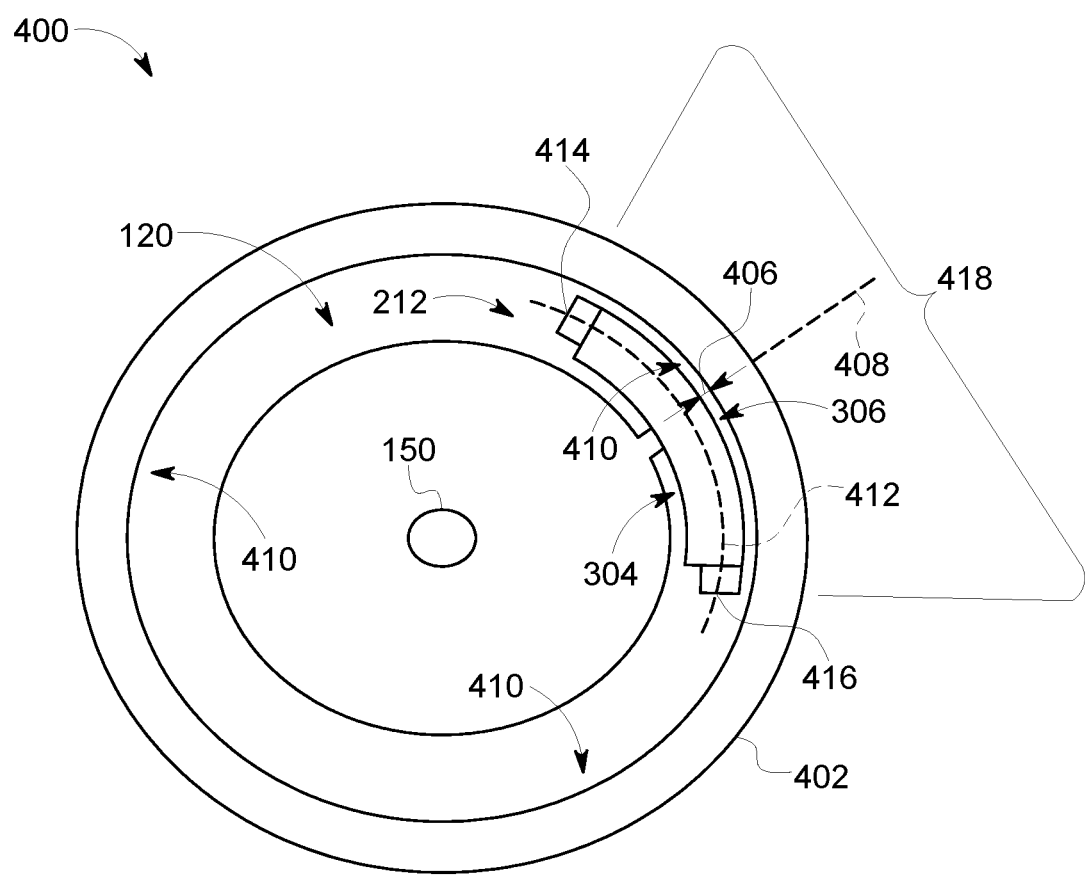
FIG. 4 illustrates a cross section of the power system of a pipeline inspection system within a pipeline, in accordance with an embodiment.

FIG. 4 illustrates a cross section 400 of the power system 120 of the PSI 100 within a pipeline 402, in accordance with an embodiment. The pipeline 402 may be electrically conductive. For example, the pipeline 402 may be comprised of steel, aluminum, and/or the like. Opposing ends 414 and 416 of the induction generator 212 extends along the radially curved plane 412. The radially curved plane 412 of the induction generator 212 may be configured to be similar to and/or the same as a curve of an inner surface area 410 of the pipeline 402. For example, the radially curved plane is aligned with the inner surface area 410 of the pipeline 402.

The radially curved plane 412 may be configured to allow the outer surface 306 of the induction generator 212 to be uniformly proximate to the pipeline 402 at a distance 406. For example, the distance 406 between the outer surface 306 and the inner surface area 410 of the pipeline 402 is approximately the same along the outer surface 306.

Additionally or alternatively, the outer surface 306 does not extend along an entire circumference of the inner surface area 410. For example, the outer surface 306 of the induction generator 212 is adjacent to a portion 418 of the circumference of the inner surface area 410 of the pipeline 402.

The distance 406 may be defined by the controller circuit 202 using a radial actuator 204 (FIG. 2). For example, the induction generator 212 may be mechanically fastened to the PSI 100 via a cylinder, which allows the induction generator 212 to move radially away or towards the support structure along an axis 408. The radial actuator 204 may be configured to adjust a radial position of the induction generator 212 along the axis 408 to adjust the distance 406.

Figure 5:
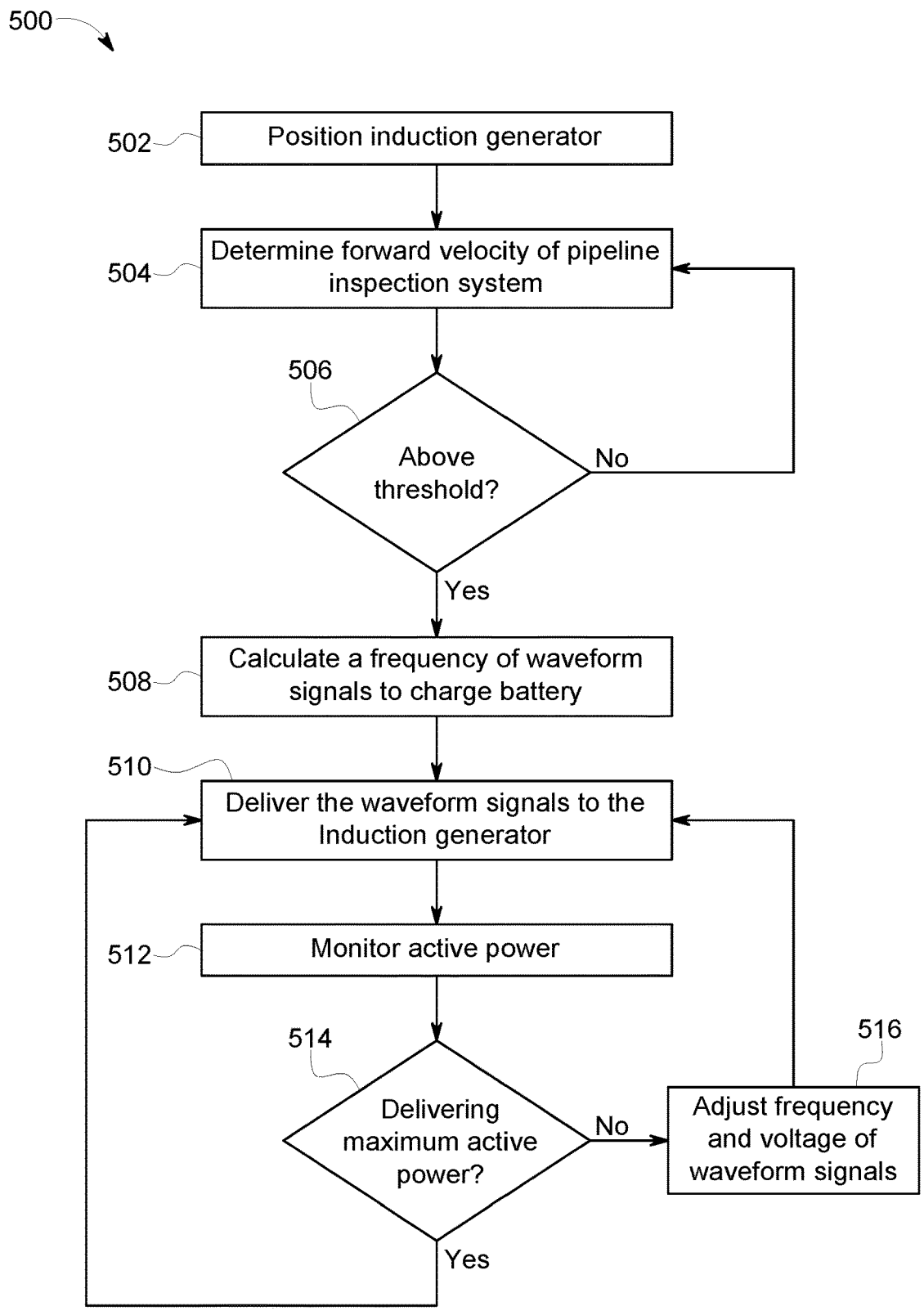
FIG. 5 illustrates a flowchart of a method for powering a pipeline inspection system, in accordance with an embodiment.

In connection with FIG. 5, the controller circuit 202 may adjust the distance 406 and/or the periodic waveforms delivered to the induction motor 212 to generate electric power to charge the battery and/or the components of the PSI 100. For example, the controller circuit 202 supplies periodic waveforms to the induction generator 212 that generate a travelling magnetic wave-field directed to the inner surface 410 of the pipeline 402. The magnetic wave-field having a different velocity (e.g., synchronous velocity) relative to a translational velocity (e.g., a forward velocity) of the PIS 100 along the pipeline 402. For example, the translational velocity is greater than the velocity of the magnetic wave-field. The relative difference in velocities between the magnetic wave-field and the translational velocity, combined with the electromagnetic force generated by the stator magnetic field and the eddy currents induced in the pipeline 402, creates electric power (e.g., active power) that can be transferred to the batteries 208.

FIG. 5 illustrates a flowchart of a method 500 for powering a pipeline inspection system, (e.g., the PIS 100, in accordance with an embodiment. The method 500, for example, may employ structures or aspects of various embodiments (e.g., systems and/or methods) discussed herein. In various embodiments, certain steps (or operations) may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. In various embodiments, portions, aspects, and/or variations of the method 500 may be used as one or more algorithms to direct hardware to perform one or more operations described herein.

Beginning at 502, the controller circuit 202 may position the induction generator 212 based on the pipeline 402. For example, the controller circuit 202 may instruct the radial actuator 240 to adjust a radial position of the induction generator 212 along the axis 408. The radial position is adjusted based on a diameter of the pipeline 402. For example, the radial actuator 240 may adjust the radial position of the induction generator 212 to be at the distance 406 from the inner surface area 410 of the pipeline 402. By adjusting the radial position of the induction generator 212, the radial actuator 240 allows the PIS 100 to be positioned in multiple pipelines having different diameters.

At 504, the controller circuit 202 may determine a forward velocity of the PIS 100. The forward velocity of the PIS 100 is based on a flow rate of the fluid within the pipeline 402 propelling the PIS 100. For example, the flow rate of the fluid within the pipeline 402 may range from 0.5 m/s to 10 m/s. The controller circuit 202 may determine a forward velocity of the PIS 100 based on one or more sensor measurements received from the sensors units 154. For example, the controller circuit 202 may determine a velocity of the PIS 100 based on a flow rate, measured by one of the sensor units 154, of the fluid traversing within the pipeline 402 and propelling the PIS 100. In another example, the controller circuit 202 may determine a velocity of the PIS 100 based on changes in positional measurements of the PIS 100 measured by one of the sensor units 154 (e.g., GPS). In another example, the controller circuit 202 may receive a sensor measurement of one of the sensor units 154 representing a velocity of the PIS 100 traversing within the pipeline 402.

At 506, the controller circuit 202 may determine if the forward velocity is above a predetermined threshold stored in the memory 206. For example, the predetermined threshold may be utilized by the controller circuit 202 to verify that the PIS 100 has a velocity greater than zero (e.g., the PIS 100 is moving within the pipeline 402).

If the forward velocity is above the predetermined threshold, then at 508 the controller circuit 202 may calculate a frequency of periodic waveform signals to charge the batteries 208. The frequency of the periodic waveform signals may be configured to generate an active power from the induction generator 212, which may be used to charge the batteries 208. As described above, active power is generated by the induction generator 212 when a velocity of the PIS 100 is greater than the velocity (e.g., synchronous velocity) of the magnetic field generated by the induction generator 212. For example, the periodic waveform signals are delivered to the windings 213-215 of the induction generator 212, which creates a magnetic field. Based on conductivity of the pipeline 402 and proximity with the induction generator 212, the magnetic field of the induction generator 212 generates eddy currents in the pipeline 402, which generates a force exerted on the induction generator 212.

The velocity (represented as the variable $v_s$) of the magnetic field is defined based on a frequency (represented as the variable f) of the periodic waveform signals and the pole pitch (represented as the variable $t_p$) as defined in Equation 1. Based on the forward velocity determined at 504, the controller circuit 202 may calculate a frequency resulting in the velocity of the magnetic field having a magnitude less than the forward velocity.

$$v_s = 2 \cdot t_p \cdot f \quad \text{(Equation 1)}$$

Figure 6:
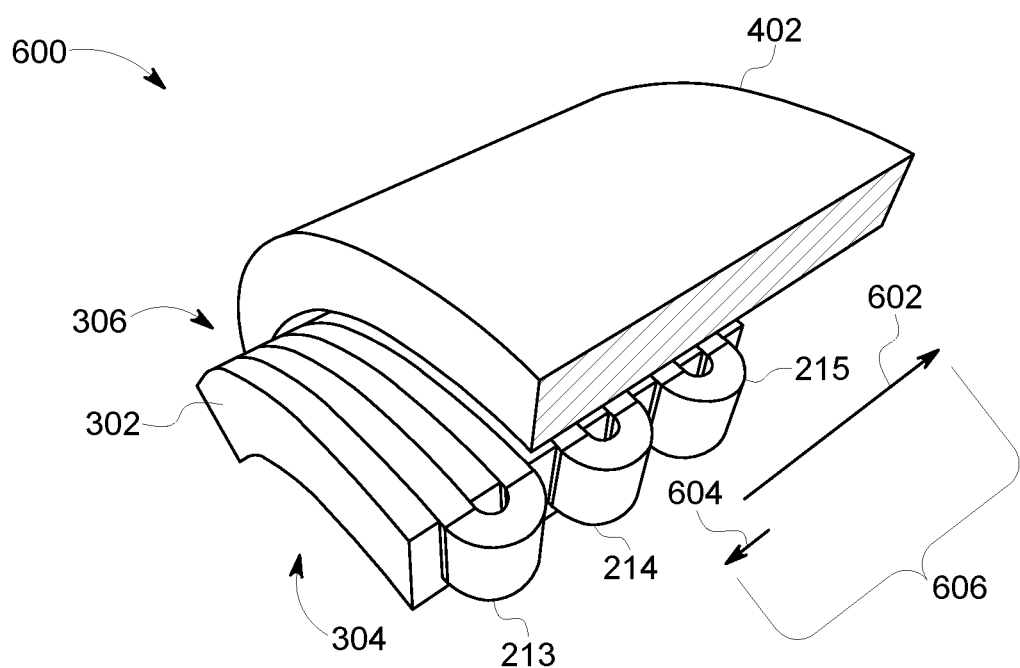
FIG. 6 illustrates a peripheral view of the induction generator shown in FIG. 3 within a portion of a pipeline, in accordance with an embodiment.

FIG. 6 illustrates a peripheral view 600 of the induction generator 212 within a portion of the pipeline 402, in accordance with an embodiment. A velocity vector 602 represents the forward velocity of the PSI 100 (e.g., determined at 504) traversing within the pipeline 402, and a velocity vector 604 represents the velocity (e.g., synchronous velocity) of the magnetic field. The controller circuit 202 may calculate the frequency of the periodic waveform signals based on a predetermined velocity gap 606 stored in the memory 206. The predetermined velocity gap 606 may represent a difference in magnitude between the velocity vector 602 and the velocity vector 604. Optionally, the predetermined velocity gap 606 may be based on a slip of the induction generator 212. Additionally or alternatively, the predetermined velocity gap 606 may be based on previous operations of the PIS 100. For example, based on a prior pipeline traversed by the PIS 100.

The controller circuit 202 may calculate the frequency of the periodic waveform signals to produce the velocity vector 604. The velocity vector 604 having a magnitude that forms the predetermined velocity gap 606 relative to the velocity vector 602. For example, as shown in FIG. 6, the controller circuit 202 may configure the periodic waveform signals based on the phases between the signals, to produce a magnetic field from the induction generator 212 resulting in a force exerted on the PIS 100 that is opposed to the direction of the velocity vector 602. Additionally or alternatively, the controller circuit 202 may determine the frequency of the periodic waveform to produce a velocity vector 604 that has a magnitude less than the magnitude of the velocity vector 602, but in the same direction.

Additionally or alternatively, the controller circuit 202 may calculate an initial voltage (e.g., amplitude), current, and/or the like of the periodic waveform signals. For example, the voltage and/or current of the periodic waveform signals effects a strength and/or amplitude of the magnetic field. The controller circuit 202 may calculate the initial voltage and/or current based on an electrical resistivity of the pipeline 402. The electrical resistivity of the pipeline 402 may be stored in the memory 206. The voltage and/or current of the periodic waveform signals adjust the amplitude of the magnetic field emitted by the induction generator 212. The controller circuit 202 may configure the initial voltage and/or current to be higher for pipelines having a higher electrical resistivity relative to pipelines traversed by the PIS 100 having a lower electrical resistivity. For example, the controller circuit 202 may calculate the initial voltage and/or current with a higher value for the pipeline 402 relative to the initial voltage and/or current of a pipeline having a higher electrical resistivity.

The frequency, voltage and/or current of the periodic waveform signals that form the predetermined velocity gap 606 may be based on an initial or starting point for the controller circuit 202 to perform a Maximum Power Point Tracking (MPPT). For example, the operations at 510, 512, 514 and 516 of the method 500 performed by the controller circuit 202 may be utilized to determine a select frequency and/or amplitude (e.g., voltage, current) of the periodic waveform signals that result in the induction generator 202 generating active power higher relative to other candidate frequencies and/or amplitudes of the periodic waveform signals.

Returning to FIG. 5 at 510, the signal generator 210 may deliver the periodic waveform signals to the induction generator 212. For example, the controller circuit 202 may instruct the signal generator 210 to generate the periodic waveform signals having the frequency determined at 510 and the initial voltage and/or current (e.g., amplitude). The signal generator 210 is electrically coupled to the windings 213-215, which may receive the periodic waveforms signals generated by the signal generator 210. The periodic waveform signals provide current to the windings 213-215 of the induction generator 212, which creates a magnetic field. The magnetic field generates eddy currents in the pipeline 402, which may generate a force opposed to the forward velocity of the PIS 100 based on the frequency determined at 510. Based on the difference in velocities, corresponding to the predetermined velocity gap 606, the induction generator 212 generates active power. The active power is utilized by the controller circuit 202 to charge the batteries 208 of the PIS 100.

At 512, the controller circuit 202 may monitor the active power generated by the induction generator 212. For example, the controller circuit 202 may measure the power of the electrical conductors (e.g., wires) electrically coupling the induction generator 212 to the signal generator 210 and/or the controller circuit 202 for a period of the periodic waveform signals.

At 514, the controller circuit 202 may determine if a maximum active power is being generated by the PIS 100. For example, the controller circuit 202 evaluates the active power being generated by the induction generator 202 relative to a prior values of the active power to configure the periodic waveform signals to operate the induction generator 212 to an active power within a predetermined threshold of a calculated maximum active power point. Additionally or alternatively, the maximum active power point may correspond to a charging threshold. The charging threshold may be based on the predetermined electrical specification (e.g., a charging current, a charging voltage) corresponding to an amount of power that can charge the batteries 208.

The controller circuit 202 may compare the active power generated by the induction generator 202 to prior active power values generated by the induction generator 202 stored in the memory 206. It may be noted for the initial active power (e.g., active power based on the periodic waveform signals calculated at 508), the prior active power value is zero. If the active power is below the prior active power value, the controller circuit 202 may determine that the maximum active power has been reached at a prior electrical configuration (e.g., frequency, voltage, current) of the periodic waveform signals and proceed to 516. If the active power is above the prior active power value, the controller circuit 202 may determine that the maximum active power has not been reached at a prior electrical configuration (e.g., frequency, voltage, current) of the periodic waveform signals and proceed to 516. If the active power is at the prior active power value and/or at the charging threshold, the controller circuit may determine that the maximum active power has been reached and proceed to 510.

At 516, the controller circuit 202 may dynamically adjust the frequency, voltage and/or current (e.g., amplitude) of the periodic waveform signals to adjust the active power generated by the induction generator 212 based on an MPPT strategy. For example, the controller circuit 202 may iteratively adjust the frequency, voltage and/or current of the periodic waveform signals by reducing the amount of adjustment of the frequency, voltage and/or current until the maximum active power is reached at 514. In another example, the controller circuit 202 may increment the frequency, voltage and/or current of the periodic waveform signals over time until the maximum active power is determined reached at 514. It may be noted that other approaches to MPPT may be performed by the controller circuit 202 as known in the art.

Additionally or alternatively, the controller circuit 202 may determine if the pipe line 402 is conductive. For example, portions of the pipeline 402 may not be composed of a conductive element, such as plastic. When the induction generator 212 is positioned at the portions of the pipeline 402 not composed of a conductive element, eddy currents would not be generated in the pipeline 402 in response to the magnetic field generated by the induction generator 212. Without the eddy currents generated within the pipeline 402, active power may not be generated by the induction generator 212. If no active power is generated, the controller circuit 202 may determine that the pipeline 402 is not conductive. For example, the controller circuit 202 may instruct the signal generator 210 to terminate the delivery of the periodic waveform signals to conserve energy of the batteries 208. Optionally, the controller circuit 202 may instruct the signal generator 210 to only deliver the periodic waveform signals during one or more test cycles, until the controller circuit 202 determines the pipeline 402 is a conductive surface. For example, during each test cycle the controller circuit 202 may measure the power of the electrical conductors (e.g., wires) electrically coupling the induction generator 212 to the signal generator 210 and/or the controller circuit 202 for a period of the periodic waveform signals. If active power is detected, then the controller circuit 202 may determine that the pipeline 402 is conductive.

In an embodiment a system (e.g., a pipeline inspection system) is provided. The system includes an induction generator extending along a radially curved plane. The induction generator having an outer surface and an opposing inner surface. The outer surface is positioned proximate to an inner surface area of a pipeline. The system also includes a controller circuit configured to generate a plurality of periodic waveform signals. The plurality of periodic waveform signals are received by the induction generator. The induction generator is configured to generate active power that charges an electric power source based on the plurality of periodic waveform signals and the inner surface area.

Optionally, a frequency of the plurality of periodic waveform signals is based on a forward velocity of a pipeline inspection system traversing within the pipeline.

Optionally, the outer surface is configured to cover a portion of a circumference of the inner surface area of the pipeline.

Optionally, the induction generator is configured to emit a magnetic field in response to the plurality of periodic waveform signals. A velocity of the magnetic field may be based on a forward velocity of a pipeline inspection system. Additionally or alternatively, the plurality of periodic waveform signals are configured based on a maximum power point tracking. Additionally or alternatively, the magnetic field is configured to generate a force exerted on the induction generator. The force may be opposed to the forward velocity.

Optionally, the system includes a radial actuator. The radial actuator may be configured to position the induction generator at a radial position relative to the inner surface area based on a diameter of the pipeline.

Optionally, the system includes a vessel having a sensor unit. The sensor unit may be configured to measure a forward velocity of the pipeline inspection system.

Optionally, the induction generator includes a magnetic core with a plurality of groves and a set of windings, each winding is positioned within a corresponding grove.

In an embodiment a method (e.g., for powering a pipeline inspection system) is provided. The method includes determining a forward velocity of a pipeline inspection system (PIS) traversing within a pipeline, calculating at least one of a frequency, voltage or current of a plurality of periodic waveform signals based on the forward velocity, and generating the plurality of periodic waveform signals. The plurality of periodic waveform signals are received by an induction generator. The induction generator extending along a radially curved plane. The induction generator having an outer surface and an opposing inner surface. The outer surface is positioned proximate to an inner surface area of the pipeline. The method further includes receiving an active power from the induction generator. The active power is based on the plurality of periodic waveform signals and the inner surface area. The method also includes utilizing at least a portion of the active power to charge an electric power source of the PIS.

Optionally, the method includes emitting a magnetic field based on the plurality of periodic waveform signals. A velocity of the magnetic field may be based on the forward velocity of the PIS. Additionally or alternatively, the magnetic field is configured to generate a force exerted on the induction generator. The force may be opposed to the forward velocity. Additionally or alternatively, the method includes positioning the induction generator at a radial position relative to the inner surface area based on a diameter of the pipeline.

Optionally, the frequency is calculated based on a maximum power point tracking.

Optionally, the method includes adjusting the frequency, voltage, or current of the plurality of periodic waveform signals based on an amount of the active power relative to a charging threshold.

Optionally, the plurality of periodic waveform signals are generated at a different phase with respect to each other.

In an embodiment a system (e.g., a pipeline inspection system) is provided. The system includes a support structure, and a plurality of vessels mechanically attached to the support structure. At least one of the vessels having a sensor unit configured to measure a forward velocity of a pipeline inspection system (PIS). The system includes a power system mechanically attached to the support structure. The power system having an induction generator extending along a radially curved plane. The induction generator having an outer surface and an opposing inner surface. The outer surface is positioned proximate to an inner surface area of a pipeline. The power system further includes a controller circuit configured to generate a plurality of periodic waveform signals. The plurality of periodic waveform signals are received by the induction generator. The induction generator is configured to generate active power that charges an electric power source based on the plurality of periodic waveform signals and the inner surface area.

Optionally, a frequency of the plurality of periodic waveform signals are based on a forward velocity of the PIS traversing within the pipeline.

Optionally, the outer surface is configured to cover a portion of a circumference of the inner surface area of the pipeline.

Optionally, the induction generator is configured to emit a magnetic field in response to the plurality of periodic waveform signals. The magnetic field may be configured to generate a force exerted on the induction generator. The force may be opposed to the forward velocity.

It should be noted that the particular arrangement of components (e.g., the number, types, placement, or the like) of the illustrated embodiments may be modified in various alternate embodiments. For example, in various embodiments, different numbers of a given module or unit may be employed, a different type or types of a given module or unit may be employed, a number of modules or units (or aspects thereof) may be combined, a given module or unit may be divided into plural modules (or sub-modules) or units (or sub-units), one or more aspects of one or more modules may be shared between modules, a given module or unit may be added, or a given module or unit may be omitted.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein. Instead, the use of "configured to" as used herein denotes structural adaptations or characteristics, and denotes structural requirements of any structure, limitation, or element that is described as being "configured to" perform the task or operation.

It should be noted that the various embodiments may be implemented in hardware, software or a combination thereof. The various embodiments and/or components, for example, the modules, or components and controllers therein, also may be implemented as part of one or more computers or processors. The computers or processors may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a solid state drive, optic drive, and the like. The storage device may also be other similar means for loading computer programs or other instructions into the computer or processor.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. Dimensions, types of materials, orientations of the various components, and the number and positions of the various components described herein are intended to define parameters of certain embodiments, and are by no means limiting and are merely exemplary embodiments. Many other embodiments and modifications within the spirit and scope of the claims will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose the various embodiments, and also to enable a person having ordinary skill in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or the examples include equivalent structural elements with insubstantial differences from the literal language of the claims.

What is claimed is:

1. A pipeline inspection system (PIS) comprising:
   an induction generator extending along a radially curved plane, the induction generator having an outer surface and an opposing inner surface, the outer surface is positioned proximate to an inner surface area of a pipeline;
   a controller circuit configured to generate a plurality of periodic waveform signals, wherein the plurality of periodic waveform signals are received by the induction generator and the induction generator is configured to generate active power that charges an electric power source based on the plurality of periodic waveform signals and the inner surface area; and
   a radial actuator configured to position the induction generator at a radial position relative to the inner surface area based on a diameter of the pipeline.

2. The PIS of claim 1, wherein a frequency of the plurality of periodic waveform signals is based on a forward velocity of the pipeline inspection system traversing within the pipeline.

3. The PIS of claim 1, wherein the outer surface is configured to cover a portion of a circumference of the inner surface area of the pipeline.

4. The PIS of claim 1, wherein the induction generator is configured to emit a magnetic field in response to the plurality of periodic waveform signals, a velocity of the magnetic field is based on a forward velocity of the pipeline inspection system.

5. The PIS of claim 4, wherein the plurality of periodic waveform signals are configured based on a maximum power point tracking.

6. The PIS of claim 4, wherein the magnetic field is configured to generate a force exerted on the induction generator, wherein the force is opposed to the forward velocity.

7. The PIS of claim 1, further comprising a vessel having a sensor unit, the sensor unit configured to measure a forward velocity of the pipeline inspection system.

8. The PIS of claim 1, wherein the induction generator includes a magnetic core with a plurality of groves and a set of windings, each winding is positioned within a corresponding grove.

9. A pipeline inspection system (PIS) comprising:
   a support structure;
   a plurality of vessels mechanically attached to the support structure, at least one of the vessels having a sensor unit configured to measure a forward velocity of a pipeline inspection system (PIS);
   a power system mechanically attached to the support structure, the power system having:
      an induction generator extending along a radially curved plane, the induction generator having an outer surface and an opposing inner surface, the outer surface is positioned proximate to an inner surface area of a pipeline; and
      a controller circuit configured to generate a plurality of periodic waveform signals, wherein the plurality of periodic waveform signals are received by the induction generator and the induction generator is configured to generate active power that charges.

10. The PIS of claim 9, wherein a frequency of the plurality of periodic waveform signals are based on a forward velocity of the PIS traversing within the pipeline.

11. The PIS of claim 9, wherein the outer surface is configured to cover a portion of a circumference of the inner surface area of the pipeline.

12. The PIS of claim 9, wherein the induction generator is configured to emit a magnetic field in response to the plurality of periodic waveform signals, wherein the magnetic field is configured to generate a force exerted on the induction generator, wherein the force is opposed to the forward velocity.

* * * * *